United States Patent [19]

Lang

[11] Patent Number: 5,306,209

[45] Date of Patent: Apr. 26, 1994

[54] CONTAMINANT SHIELD FOR VIEWING PORTS

[76] Inventor: Fred D. Lang, 1662 El Padro, Livermore, Calif. 94550

[21] Appl. No.: 877,632

[22] Filed: May 4, 1992

[51] Int. Cl.⁵ .............................................. F24F 9/00
[52] U.S. Cl. ...................................... 454/192; 432/32; 454/188
[58] Field of Search ...................... 454/188, 190, 192; 432/32, 64

[56] References Cited

U.S. PATENT DOCUMENTS

| | | | |
|---|---|---|---|
| 2,896,854 | 7/1959 | Noble et al. | 454/188 X |
| 3,387,551 | 6/1968 | Hughes | 454/188 X |
| 3,473,905 | 10/1969 | Jago et al. | 454/188 X |
| 3,575,398 | 4/1971 | Lincoln et al. | 454/188 X |
| 4,074,620 | 2/1978 | Jansson | 454/192 X |

FOREIGN PATENT DOCUMENTS

| | | | |
|---|---|---|---|
| 1955660 | 5/1971 | Fed. Rep. of Germany | 432/64 |
| 1554724 | 10/1979 | United Kingdom | 454/188 |

*Primary Examiner*—Harold Joyce
*Attorney, Agent, or Firm*—Howard E. Sandler; Stephen Donovan

[57] ABSTRACT

A dirt shield for viewing ports of contaminated environments which includes the formation of a cone of flowing gas disposed in front of the window of the port combined with a flow of ionized gas under pressure in front of the window between the window and the cone of gas.

9 Claims, 3 Drawing Sheets

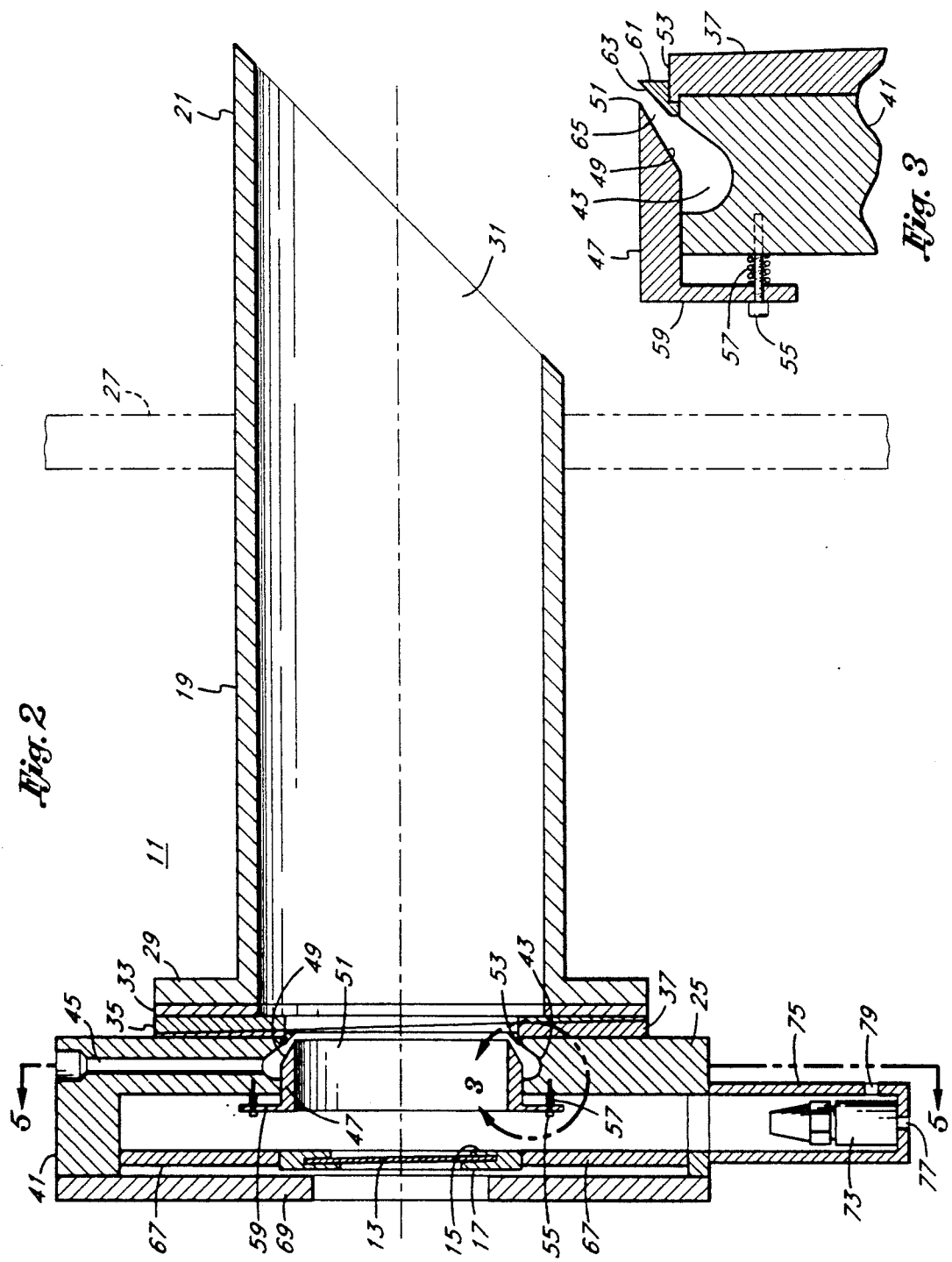

CONTAMINANT SHIELD FOR VIEWING PORTS

BACKGROUND OF THE INVENTION

1. Field of the Invention

The present invention relates to viewing ports for contaminated environments, and more particularly to a dirt shield for a viewing port which prevents contaminants or particulates from adhering to the viewing window of the port.

2. Description of the Prior Art

There are many applications for the use of a viewing port with respect to contaminated or hostile environments for the purpose of taking measurements or observing the internal conditions or change of the environment. Examples of such situations include smoke stacks, steel producing retorts, and chemical reaction vessels. In many applications, in addition to viewing internal conditions, measurements are made across the contaminated space by using transmitted light or radiation. It is the purpose of the viewing port to isolate from the contaminated environment the instruments or persons which take the measurements or make the observations.

The present industrial technique for maintaining a clean instrument optical lens, or viewing windows of a port, involves simply the use of a purging gas inletted around the window of the port. If the contamination is light, such techniques may be effective. However, for environments which have a high soot or ash content, as is associated with the combustion of coal in a fossil-fired commercial power or steam generation plant, the technique is insufficient. It is necessary to schedule frequent manual cleanings of the view port windows. Such cleanings can cause disruption of the instrument operation or possibly cause damage to the window itself. In addition, such cleanings are costly and render the instruments ineffective during the period of time that it takes for the cleaning operation to be completed.

The present invention provides a dirt shield for viewing ports which includes the formation of a cone of flow of gas disposed in front of the window of the port combined with a flow of ionized gas between the window and the cone of gas.

SUMMARY OF THE INVENTION

The present invention is a dirt shield for a viewing port of a contaminated environment. It is comprised of a window in the view port. A means is provided for forming a cone of flowing gas disposed between the window and the environment with the apex of the cone of gas flow being formed to flow toward the contaminated environment. A means is provided for establishing the window and all internal surfaces of the view port disposed between the window and the cone of gas, and all particulate contaminants which enter the space between the window and the cone of gas, at neutral electrical potential.

The means for forming the cone of flowing gas includes injecting gas at high pressure into the environment through an annular nozzle disposed between the window of the port and the environment. The means for establishing the window and the internal surfaces of the port disposed in the space between the window and the cone of gas, and all particulate contaminants in that space, at neutral electrical potential, includes supplying a separate flow of ionized gas into that space.

OBJECTS OF THE INVENTION

It is therefore an important object of the present invention to provide a dirt shield for a viewing port of a contaminated environment.

It is another object of the present invention to provide a cone of flowing gas for a viewing port for a contaminated environment which in its operative position is disposed between the window and the environment.

It is a further object of the present invention to provide a flow of gas for a viewing port of a contaminated environment which establishes the internal surfaces of the view port, the window, and the particulate contaminants at a neutral electrical potential.

And it is a further object of the present invention to provide a dirt shield for a viewing port of a contaminated environment which eliminates the need for the viewing window to be removed for cleaning.

Other objects and advantages of the present invention will become apparent when the apparatus of the present invention is considered in conjunction with the accompanying drawings.

DESCRIPTION OF THE DRAWINGS

FIG. 2 is a sectional view showing the assembled invention;

FIG. 3 is a broken out detail in cross-section of the gas outlet of the annular nozzle assembly of FIG. 2;

DESCRIPTION OF THE PREFERRED EMBODIMENT

Reference is made to the drawings for a description of the preferred embodiment of the present invention wherein like reference numbers represent like elements on corresponding views.

Figure 1:
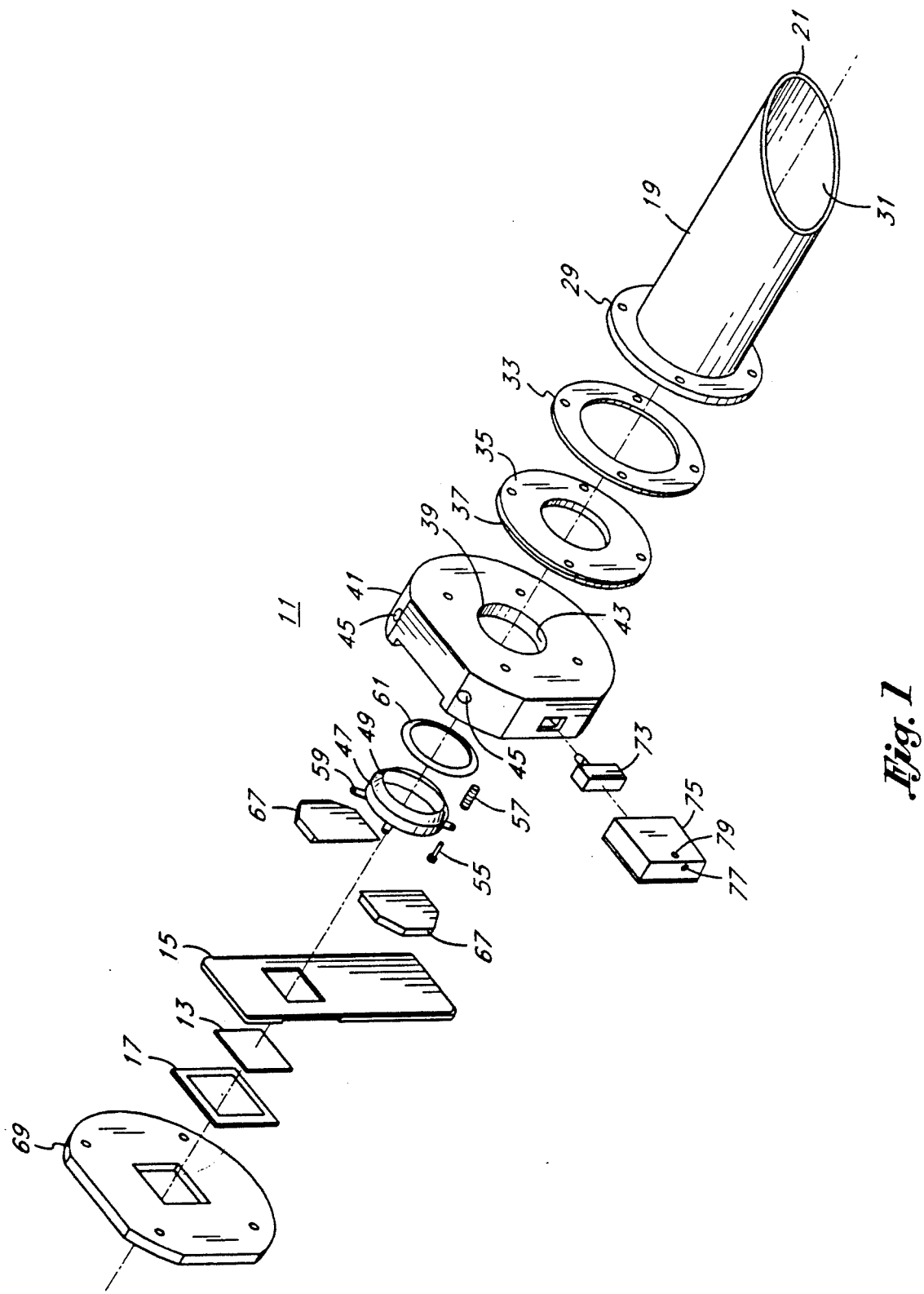
FIG. 1 is an exploded perspective view of the present invention.

Reference is made to the exploded view FIG. 1 wherein the individual elements of the viewing port assembly 11 can be considered and to FIG. 2 wherein the assembly of the elements is illustrated. The window 13 of the viewing port is held in a removable mounting frame 15 which has an elongated configuration. The window is held in place by a locking frame 17 which secures to the larger mounting frame. The viewing port assembly includes a hollow shroud 19 having a first end 21 disposed in the contaminated environment with the viewing window disposed at the other end thereof in spaced relation thereto and exposed to the environment.

Figure 4:
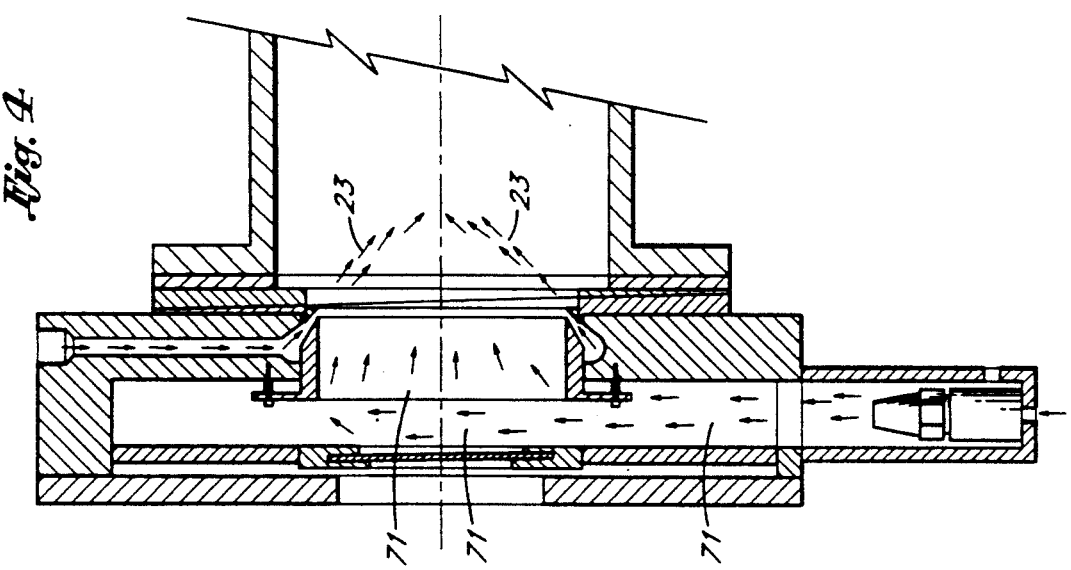
FIG. 4 is a broken art detail of FIG. 2 with a schematic gas flow diagram for the annular nozzle and the gas ionizer.

A means is provided for forming a cone of flowing gas 23 disposed between the window 13 of the viewing port 11 and the contaminated environment with the apex of the cone of gas flow being formed to flow toward the environment. This gas flow is illustrated in FIG. 4. In the preferred embodiment of the invention, the means for forming the cone of gas includes injecting the selected gas at pressure into the environment through an annular nozzle which is disposed between the window and the environment. The annular nozzle assembly 25 for forming the cone of gas is secured to the shroud 19 that projects into the environment. The shroud 19 is preferably made of stainless steel for corrosion resistance and is secured in place in the environment containment vessel wall 27 usually by welding. The annular nozzle assembly 25 which is disposed between the window 19 and the shroud 19 is particularly designed to release a flow of gas in a pattern which creates a cone of gas flow.

The shroud 19 in its simplest form is a flanged pipe 29 having a beveled open first end 21 which projects into the contaminated flow. The non-beveled side is positioned toward the contaminated flow to shield the shroud outlet therefrom as viewed in FIG. 2. The shroud is a hollow tube which forms an internal passageway 31 for the passage of light or radiation to permit the viewing which occurs or for the measurement beams which are projected therethrough. The nozzle assembly is mounted to the shroud by means of a gasket 33 which abuts a pair of beveled adjusting rings 35, 37. These rings are tapered into a bevel to allow alignment of the window 13 with the center bore of the shroud. Rotation of the tapered rings with respect to each other changes the angulation of the nozzle with respect to the shroud, and by rotating the rings the desired alignment is achieved.

Figure 5:
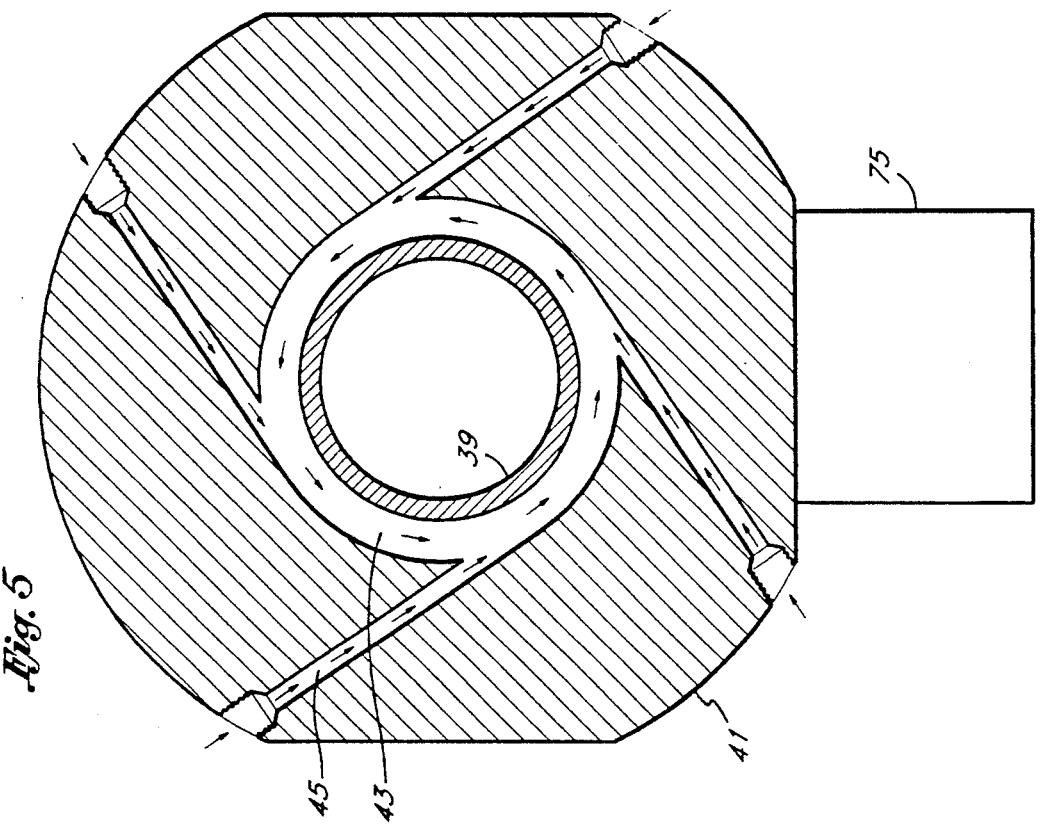
FIG. 5 is a cross-sectional view of the annular nozzle taken along lines 5—5 of FIG. 2.

Reference is made to FIGS. 2, 3 and 5 for an understanding of the internal construction of the annular nozzle. The nozzle includes a circular opening 39 formed in the nozzle body 41 which is aligned with the window 13 of the viewing port and the centerbore of the internal passageway 31 of the shroud 19. The operative portion of the nozzle body includes an annular channel 43 which forms part of the circular opening. This channel forms a portion of the cavity which comprises the gas release valve.

A means is provided for supplying gas to the annular nozzle at a pressure high enough to cause said cone of gas flow 23 to form when the gas is released through the nozzle into the contaminated environment. These means include at least two passageways 45 formed in the nozzle body 41 which communicate with the annular channel 43 formed in the circular opening 39 of the annular nozzle. These passages are arranged to deliver the gas into the channel at a multiple of locations which are symmetrically arranged around the channel to provide as even a gas flow distribution around the channel as possible whereby the gas exits the channel approximately at the same flow rate and pressure therearound to form a symmetric cone of gas flow. To enhance the flow distribution, the channels are angulated with respect to the annular channel whereby the gas is inletted tangentially to the channel.

A first ring member 47 is provided which has a tapered external surface 49 which forms a sharp edge 51 on the outer periphery thereof. The ring member is adjustably secured in the circular opening 39 of the nozzle to cover a substantial portion of the channel 43 to enclose the open side of it. The tapered surface 49 is disposed in opposed relation to the edge 53 of the annular channel which is closest to the contaminated environment whereby the first ring member 47 in conjunction with the annular channel 43 forms a controllable outlet or valve for the flow of gas 23 from the nozzle which depends on the positioning of the ring member with respect to the channel. This is most clearly illustrated in FIG. 3 The first ring member in the preferred embodiment of the present invention is secured by means of screws 55 and springs 57 which project through tabs 59 secured to the ring member whereby the actual positioning of the ring member can be adjusted with respect to the annular channel 43. The ring member could actually be screwed into the circular opening 39 to achieve this adjustment but that is a more expensive mode of construction.

The nozzle assembly 25, for ease of construction, also includes a second tapered ring member 61 which is seated in the annular channel 43 at the exit edge 53 thereof forming the opposite edge of the controllable outlet or valve. The configuration of this ring is also most easily viewed in FIG. 3. The second ring member has a tapered internal surface 63 disposed in opposed relation to the tapered external surface 49 of the first ring member 47 forming a slot 65 therebetween which can be widened or narrowed depending upon the positioning of the ring member in the circular opening at the nozzle body. In this arrangement, the air passes between the two ring members 47, 61 to exit the annular nozzle and form the gas flow cone 23. This second tapered ring member can be eliminated simply by properly forming the edge of the annular channel 43 in the nozzle to create a tapered valve seat.

The window mounting frame 15 is arranged to slide up and down in the annular nozzle body 41 so that it can be removed for adjustment or possibly cleaning in the event air pressure is lost in the annular nozzle for some reason and dirt accumulates on the window 13. Sealing plates 67 are provided which seal the sliding frame 15 in the annular nozzle and a rear cover plate 69 secures to the annular nozzle case to hold the pieces in position.

A means is provided for establishing the window 13 of the viewing port, all internal surfaces of the port disposed between the window and the cone of gas flow 23, and the particulate contaminants which enter the space between the window and the cone of gas, at neutral electrical potential. This is accomplished by providing a means for supplying a flow of ionized gas 71 into the space disposed between the viewing port window and the location of the cone of flow of gas when it is established as a result of gas being released through the nozzle. This gas flow is illustrated in FIG. 4. The means includes a gas ionizer 73 which is positioned on the nozzle body 41 to inject the ionized gas into the annular nozzle. The ionizer employed is a commercially available unit known as a type HS from SIMCO Company of Hatfield, Pa. The gas flows through a high voltage arc of electricity in the ionizer and then into the aforedescribed space for the purpose of establishing a neutral electrical potential on the window, the surfaces of the annular nozzle disposed between the window and the position of the gas flow cone, and the particulate contaminants which enter that space.

The gas ionizer 73 is mounted in a sealed box 75 which is attached to the annular nozzle body 41 and has an inlet means 77 for attaching the gas supply to the ionizer and an electrical feedthrough 79 to permit the electrical wires to project through the box in sealed relation and attach to the ionizer. The gases that are most commonly used for the gas flow cone and the ionized gas flow are air or nitrogen, but any inert gas such as argon or helium could be used except for the expense for those gases which is quite high.

The gas flow through the annular nozzle 25 is preferably at a pressure of from 60 to 120 psig and at a flow rate of at least 100 cubic feet per hour. The air pressure is as high as possible and usually depends upon what is available locally to the installation. Preferably it would be at 100 psig or higher. The gas pressure for the ionizer 73 is likewise desired to be between 60 and 120 psig and a flow rate of at least 60 cubic feet per hour. Again, the preferred pressure range would be approximately 100 psig or higher at the same rate of flow. In the preferred embodiment of the invention, when the two gas flows are established at the rates and velocities described herein, the soot and/or ash which exists in the contaminated environment will not adhere to the windows of the view port.

Thus it will be seen from the foregoing description of the preferred embodiment, that all of the objects and advantages are achieved. While the preferred embodiment of the invention has been described in considerable detail herein, the invention is not to be limited to such details as have been set forth except as may be necessitated by the appended claims.

I claim:

1. A dirt shield for a viewing port of a contaminated environment comprising
   a window in said port,
   a means for creating a first gas flow between said window and said environment which flows from the region in front of said window toward said environment, and
   a means for establishing said window, all internal surfaces of said port disposed between said window and said first gas flow, and all particulate contaminants which enter the space between said window and said first gas flow at neutral electrical potential.

2. The dirt shield of claim 1 wherein said means for establishing said window, said surfaces, and said contaminants at neutral electrical potential includes supplying a separate flow of ionized gas into the space disposed between said window and said first gas flow.

3. The dirt shield of claim 1 wherein said means for creating said first gas flow includes means for injecting said gas at high pressure into said environment through an annular nozzle to form a cone of gas which is disposed between said window and said environment.

4. The dirt shield of claim 1 wherein said means for creating a first gas flow includes means for forming a converging cone of flowing gas disposed with an apex of said cone being pointed toward the environment.

5. A dirt shield for a viewing port of a contaminated environment comprising
   a hollow view port shroud having a first end disposed in said environment and a viewing window disposed at the other end thereof in spaced relation thereto and exposed to said environment,
   an annular nozzle assembly secured to said shroud and disposed between said window and said shroud and formed to release a flow of gas in a pattern which creates a cone of gas flow in front of said window which flows with the apex of said cone aimed into said shroud,
   a means for supplying gas to said nozzle at a pressure high enough to cause said cone of gas flow to form when the gas is released through said nozzle into said environment, and
   a means for supplying a flow of ionized gas to the window and to the surfaces of said nozzle and any particulate contaminants disposed between said window and the location of the cone of flow of gas when it is established as a result of gas being released through said nozzle.

6. The dirt shield of claim 5 wherein said nozzle includes passages which deliver gas to an annular channel which forms part of a circular opening formed in said nozzle, said passages delivering gas to said annular channel at locations which are symmetrically arranged around said channel, and said circular opening being aligned with said window and the centerbore of said hollow internal passageway of said shroud, and
   a first ring member having a tapered external surface which forms a sharp edge on the outer periphery thereof, said ring member being adjustably secured in the circular opening of said nozzle to cover a substantial portion of said channel to enclose it, said tapered surface being disposed in opposed relation to an edge of said annular channel whereby said ring member in conjunction with said channel forms a controllable outlet for the flow of gas from said nozzle depending upon the positioning of the sharp edge of said ring member with respect to said channel.

7. The dirt shield of claim 6 wherein the passages are angulated with respect to said annular channel to inlet the gas into the channel in a flow which is tangential thereto.

8. The dirt shield of claim 5 including adjusting rings having tapered surfaces and being disposed between said shroud and said nozzle assembly to allow alignment of said window with the centerbore of said shroud.

9. A dirt shield for a viewing port of a contaminated environment comprising
   a hollow view port shroud having a first end disposed in said environment and a viewing window disposed at the other end thereof in spaced relation thereto and exposed to said environment, said window being mounted in a frame which is removably sealed to said shroud,
   an annular nozzle assembly secured to said shroud and disposed between said window and said shroud and formed to release a flow of gas in a pattern which creates a cone of gas flow in front of said window which flows with the apex of said cone aimed into said shroud,
   a circular opening formed in said nozzle and being aligned with said window and the centerbore of said hollow internal passageway of said shroud,
   internal passages in said nozzle which deliver gas to an annular channel which forms part of the circular opening at locations which are symmetrically arranged around said channel and inlet the gas tangentially thereto,
   a first ring member having a tapered external surface which forms a sharp edge on the outer periphery thereof, said ring member being adjustably secured in the circular opening of said nozzle to cover a substantial portion of said channel to enclose it, said tapered surface being disposed in opposed relation to an edge of said annular channel whereby said ring member in conjunction with said channel forms a controllable outlet for the flow of gas from said nozzle depending upon the positioning of the sharp edge of said ring member with respect to said channel,
   a means for supplying gas to said nozzle at a pressure high enough to cause said cone of gas flow to form when the gas is released through said nozzle into said environment,
   a means for supplying a flow of ionized gas to the window and to the surfaces of said nozzle and any particulate contaminants disposed between said window and the location of the cone of flow of gas when it is established as a result of gas being released through said nozzle, and
   a pair of adjusting rings having tapered surfaces and being disposed between said shroud and said nozzle assembly to allow alignment of said window with the centerbore of said shroud.

* * * * *